United States Patent
Liu

(10) Patent No.: US 9,617,578 B2
(45) Date of Patent: Apr. 11, 2017

(54) SENSOR MEMBRANE WITH LOW TEMPERATURE COEFFICIENT

(71) Applicant: Verily Life Sciences LLC, Mountain View, CA (US)

(72) Inventor: Zenghe Liu, Alameda, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 431 days.

(21) Appl. No.: 14/098,806

(22) Filed: Dec. 6, 2013

(65) Prior Publication Data

US 2015/0159190 A1 Jun. 11, 2015

(51) Int. Cl.
*G01N 27/327* (2006.01)
*C12Q 1/00* (2006.01)
(Continued)

(52) U.S. Cl.
CPC ............ *C12Q 1/006* (2013.01); *A61B 5/1486* (2013.01); *A61B 5/14532* (2013.01); *A61B 5/6821* (2013.01); *C12Q 1/002* (2013.01)

(58) Field of Classification Search
CPC G01N 27/327–27/3272; G01N 27/333; C12Q 1/002; A61B 5/1468; A61B 5/1486
See application file for complete search history.

(56) References Cited

U.S. PATENT DOCUMENTS 5,102,552 A 4/1992 Callahan et al.
5,928,918 A 7/1999 Offenbacher
(Continued)

FOREIGN PATENT DOCUMENTS

JP 2005/315871 A 11/2005
WO 93/22039 A1 11/1993
(Continued)

OTHER PUBLICATIONS

MedlinePlus Medical Encyclopedia entry Blood sugar test—blood downloaded from https://www.nlm.nih.gov/medlineplus/ency/article/003482.htm on Apr. 22, 2016.*
(Continued)

*Primary Examiner* — Alexander Noguerola
(74) *Attorney, Agent, or Firm* — McDonnell Boehnen Hulbert & Berghoff LLP

(57) ABSTRACT

An analyte sensor for measuring physiological parameters, a method for making the analyte sensor, and method of measuring a level of an analyte in a subject are disclosed. In one aspect, the analyte sensor includes a crosslinked, hydrophilic copolymer in contact with a surface of an electrode, and an analyte sensing component embedded within the crosslinked, hydrophilic copolymer. The crosslinked, hydrophilic copolymer has methacrylate-derived backbone chains of first methacrylate-derived units, second methacrylate-derived units and third methacrylate-derived units. The first and second methacrylate-derived units have side chains that can be the same or different, and the third methacrylate-derived units in different backbone chains are connected by hydrophilic crosslinks. The crosslinked, hydrophilic copolymer has an analyte permeability that is substantially temperature independent. The analyte sensor generates signals that are substantially temperature independent over a range of temperatures.

13 Claims, 7 Drawing Sheets

(51) Int. Cl.
　　　*A61B 5/145*　　(2006.01)
　　　*A61B 5/1486*　(2006.01)
　　　*A61B 5/00*　　　(2006.01)

(56) References Cited

U.S. PATENT DOCUMENTS

| | | | |
|---|---|---|---|
| 5,985,129 | A | 11/1999 | Gough |
| 6,653,358 | B2 | 11/2003 | Bruza |
| 6,927,246 | B2 | 8/2005 | Noronha |
| 7,450,980 | B2 | 11/2008 | Kawanishi |
| 7,731,835 | B2 | 6/2010 | Buck |
| 8,224,414 | B2 | 7/2012 | Kellogg |
| 8,268,637 | B2 | 9/2012 | Cunningham |
| 8,274,021 | B2 | 9/2012 | Wang |
| 8,385,998 | B2 | 2/2013 | Zhang |
| 8,437,829 | B2 | 5/2013 | Mao |
| 8,473,222 | B2 | 6/2013 | Romey |
| 8,542,024 | B2 | 9/2013 | Potyrailo |
| 2004/0185568 | A1 | 9/2004 | Matsumoto |
| 2005/0118204 | A1* | 6/2005 | Sakamoto ............ C12N 5/0641 424/400 |
| 2007/0244379 | A1 | 10/2007 | Boock et al. |
| 2008/0223732 | A1 | 9/2008 | Hodges |
| 2008/0241892 | A1 | 10/2008 | Roitman et al. |
| 2010/0096277 | A1 | 4/2010 | Abu Bakar et al. |
| 2011/0136929 | A1 | 6/2011 | Chow et al. |
| 2011/0152654 | A1 | 6/2011 | Wang et al. |
| 2011/0308944 | A1 | 12/2011 | Katsuki |
| 2012/0028283 | A1 | 2/2012 | Hoss |
| 2012/0088997 | A1 | 4/2012 | Guiseppi-Elie et al. |
| 2012/0186997 | A1* | 7/2012 | Li ............................ C12Q 1/00 205/778 |
| 2012/0245444 | A1 | 9/2012 | Otis |
| 2013/0011460 | A1 | 1/2013 | Liu |
| 2013/0084649 | A1 | 4/2013 | Crane |
| 2013/0267802 | A1 | 10/2013 | Markle |

FOREIGN PATENT DOCUMENTS

| | | |
|---|---|---|
| WO | 2005114720 A2 | 12/2005 |
| WO | 2010057095 A2 | 5/2010 |
| WO | 2012015941 A1 | 2/2012 |
| WO | 2012/115501 A1 | 8/2012 |

OTHER PUBLICATIONS

International Search Report and Written Opinion, PCT/US2014/065905, Mar. 27, 2015, pp. 1-10.

Manias, E. et al., "Temperature-Responsive Polymers for Biological Applications", Materials Research Society, 2004, vol. 785.

Ward, Mark A. et al., "Thermoresponsive Polymers for Biomedical Applications", Polymers, Aug. 3, 2011, vol. 3, pp. 1215-1242.

Non-final Office Action received from the United States Patent and Trademark Office dated Oct. 28, 2016, for U.S. Appl. No. 14/098,790.

\* cited by examiner

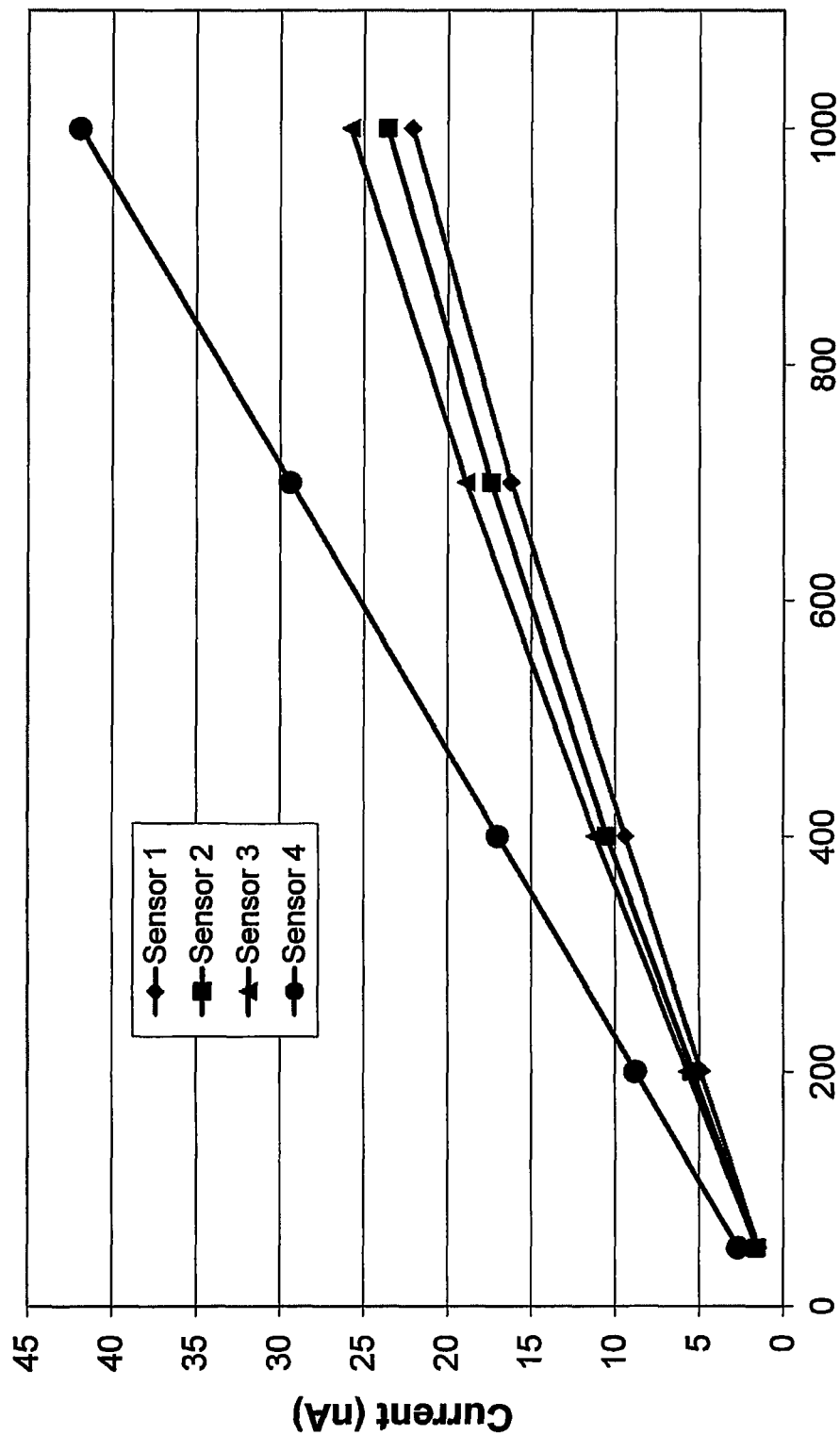

SENSOR MEMBRANE WITH LOW TEMPERATURE COEFFICIENT

BACKGROUND

Unless otherwise indicated herein, the materials described in this section are not prior art to the claims in this application and are not admitted to be prior art by inclusion in this section.

The continuous or semi-continuous monitoring of physiological parameters has applications in many areas of modern medicine. Electrochemical-based sensors are believed to be particularly suitable for the monitoring and quantification of analytes (e.g., glucose) in bodily fluid samples (e.g., blood, tear film, urine or interstitial fluid samples). The use of an electrochemical-based sensor that employs an analyte sensing component, (e.g., an enzyme) in conjunction with an electrode(s) allows for the quantification of an analyte in a liquid sample by detecting the product(s) produced from the reaction of the analyte sensing component and the analyte.

SUMMARY

In one aspect, an analyte sensor is disclosed. The analyte sensor includes a crosslinked, hydrophilic copolymer in contact with a surface of an electrode, and an analyte sensing component embedded within the crosslinked, hydrophilic copolymer. The crosslinked, hydrophilic copolymer has methacrylate-derived backbone chains of first methacrylate-derived units, second methacrylate-derived units and third methacrylate-derived units. The first and second methacrylate-derived units have side chains that can be the same or different, and the third methacrylate-derived units in different backbone chains are connected by hydrophilic crosslinks. The crosslinked, hydrophilic copolymer network has an analyte permeability that is substantially temperature independent. The analyte sensor generates signals that are substantially temperature independent over a range of temperatures.

In another aspect, a method for forming an analyte sensor is disclosed. The method involves forming mixture including the precursor components of the sensor, depositing the mixture onto a surface of an electrode, and curing the deposited mixture. The mixture includes an analyte sensing component, a first methacrylate monomer having a first hydrophilic side chain, a dimethacrylate monomer, an initiator, and a second methacrylate monomer having a second hydrophilic side chain. The crosslinked, hydrophilic copolymer has an analyte permeability that is substantially temperature independent. The analyte sensor generates signals that are substantially temperature independent over a range of temperatures.

In another aspect, a method for measuring the level of an analyte in a subject is provided which includes: (a) positioning at least a portion of an analyte sensor on a subject, wherein the analyte sensor comprises a crosslinked, hydrophilic copolymer in contact with a surface of an electrode. The analyte sensing component embedded within the crosslinked, hydrophilic copolymer, wherein the crosslinked, hydrophilic copolymer comprises backbone chains comprising; first methacrylate-derived units, each having a first hydrophilic side chain; second methacrylate-derived units, each having a second hydrophilic side chain, wherein the first and second side chains are the same or different; third methacrylate-derived units; and hydrophilic crosslinks between third methacrylate-derived units in different backbone chains; and (b) determining the level of an analyte over a period of time from signals generated by the analyte sensor, wherein the crosslinked, hydrophilic copolymer has an analyte permeability that is substantially temperature independent and wherein the analyte sensor generates signals that are substantially temperature independent over a range of temperatures.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2(b) illustrates the linear relationship between current and glucose concentration that was observed for all four analyte sensors.

DETAILED DESCRIPTION

Figure 1:
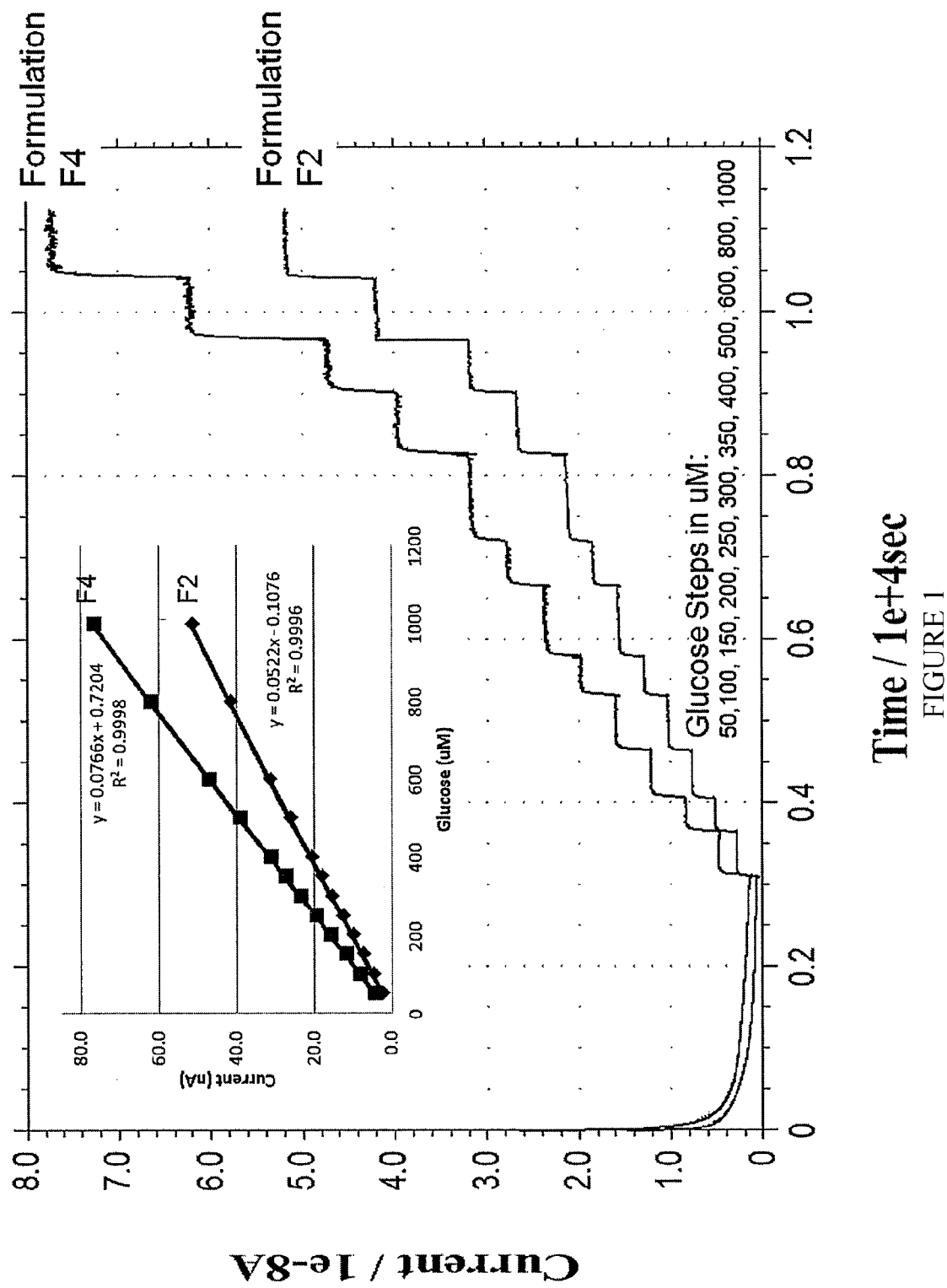
FIG. 1 is a graph of current produced by two example glucose sensors at glucose concentrations of 20 μM to 1,000 μM in phosphate buffered saline (PBS). A linear relationship between current and glucose concentration was observed (see inset graph).

The following detailed description describes various features and functions of the disclosed systems and methods with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

In many instances, regularly monitoring the concentration of a particular analyte in a fluid is beneficial. In patients suffering from diabetes mellitus, for example, where insufficient production of insulin prevents normal regulation of blood sugar levels, careful monitoring of blood glucose levels on a daily basis is required for treatment purposes. Existing systems that allow for continuous monitoring of blood glucose levels typically include implantable electrochemical sensors that typically include a diffusion-limiting membrane layer for regulating or limiting the flux of glucose into the sensor to prevent saturation occurring due to high concentrations of glucose in the bodily fluid. When such sensors become saturated, the measured output signal is no longer controlled by the flux of glucose and is no longer linearly proportional to the flux or concentration of glucose. That is, the current no longer increases linearly with the glucose concentration and increases less and less for a given increment of glucose concentration. The diffusion-limiting membrane layer functions to prevent sensor oversaturation and effectively resolves an increase in glucose concentration when concentration levels are high. However, the permeability of typical diffusion-limiting membrane layers are temperature dependent, such that a change in temperature at the sensor results in a change in the signal generated by the sensor even when the analyte concentration remains unchanged. While signal changes can be compensated for mathematically by measuring the temperature, such measurements may be difficult to do and would require the use of additional components such as thermistor. It has been determined that certain hydrophilic co-polymer membranes having a controlled temperature response in aqueous solutions can be beneficially applied in making analyte sensors that generate signals that are substantially temperature independent over a range of temperatures. Such analyte sensors can be beneficially used in continuous monitoring a level of an analyte in a subject without the need to compensate for signal changes over a range of temperatures.

Thus, in one aspect, an analyte sensor is disclosed. The analyte sensor includes: a crosslinked, hydrophilic copolymer in contact with a surface of an electrode; and an analyte sensing component embedded within the crosslinked, hydrophilic copolymer, where the crosslinked, hydrophilic copolymer includes:
  backbone chains having
    first methacrylate-derived units, each having a first hydrophilic side chain;
    second methacrylate-derived units, each having a second hydrophilic side chain,
  where the first and second side chains are the same or different;
    third methacrylate-derived units; and
  hydrophilic crosslinks between third methacrylate-derived units in different backbone chains, wherein the crosslinked, hydrophilic copolymer has an analyte permeability that is substantially temperature independent and wherein the analyte sensor generates signals that are substantially temperature independent over a range of temperatures.

In some embodiments, the analyte sensor is an enzyme-based biosensor. These devices are able to convert an analyte-concentration-dependent biochemical reaction signal into a measurable physical signal, such as an optical or electrical signal. The biosensors can be used in the detection of analytes in clinical, environmental, agricultural and biotechnological applications. Analytes that can be measured in clinical assays of fluids of the human body include, for example, glucose, lactate, cholesterol, bilirubin, proteins, lipids and electrolytes. The detection of analytes in biological fluids, such as blood, tear film, or intestinal fluid, can be important in the diagnosis and the monitoring of many diseases.

In some embodiments, the analyte sensor can be a component of a body-mountable device, such as an eye-mountable, tooth-mountable, or skin-mountable device. The eye-mountable device can be configured to monitor health-related information based on one or more analytes detected in a tear film (the term "tear film" is used herein interchangeably with "tears" and "tear fluid") of a user wearing the eye-mountable device. For example, the eye-mountable device can be in the form of a contact lens that includes a sensor configured to detect one or more analytes (e.g., glucose). The eye-mountable device can also be configured to monitor various other types of health-related information.

In some embodiments, the body-mountable device may comprise a tooth-mountable device. The tooth-mountable device may take the form of or be similar in form to the eye-mountable device, and be configured to detect at least one analyte in a fluid (e.g., saliva) of a user wearing the tooth-mountable device.

In some embodiments, the body-mountable device may comprise a skin-mountable device. The skin-mountable device may take the form of or be similar in form to the eye-mountable device, and be configured to detect at least one analyte in a fluid (e.g., perspiration, blood, etc.) of a user wearing the skin-mountable device.

The sensor as described herein can include one or more conductive electrodes through which current can flow. Depending on the application, the electrodes can be configured for different purposes. For example, a sensor can include a working electrode, a reference electrode, and a counter-electrode. Also possible are two-electrode systems, in which the reference electrode serves as a counter-electrode. The working electrode can be connected to the reference electrode via a circuit, such as a potentiostat.

The electrode can be formed from any type of conductive material and can be patterned by any process that be used for patterning such materials, such as deposition or photolithography, for example. The conductive materials can be, for example, gold, platinum, palladium, titanium, carbon, copper, silver/silver-chloride, conductors formed from noble materials, metals, or any combinations of these materials. Other materials can also be envisioned.

The crosslinked, hydrophilic copolymer of the analyte sensor includes backbone chains of methacrylate-derived units, and an analyte sensing component, such as an enzyme, embedded within the copolymer. Each of the first and second methacrylate-derived units of the backbones are covalently bound independently to first and second hydrophilic side chains, respectively. Each of the third methacrylate-derived units is covalently bound through a linker to another third methacrylate-derived unit in a different backbone chain. The crosslinks, or groups through which the third methacrylate-derived units are connected, are discussed in greater detail below. Various conformations and compositions of the side chains of the first and second methacrylate-derived units, and the crosslinks of the third methacrylate-derived units can be used to adjust the properties of the crosslinked, hydrophilic copolymer as desired, which include hydrophilicity, permeability and the ability to immobilize an analyte sensing component.

The side chains of the first and second methacrylate-derived units are hydrophilic, and can be water soluble or soluble in a water-miscible solvent, such as an alcohol. The side chains can have one or more heteroatoms, for example, nitrogen, oxygen or sulfur atoms. In some embodiments, the side chains have one or more hydroxy groups.

In some embodiments, the side chains of the first and second methacrylate-derived units include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the side chains is a block copolymer including blocks of two or three different poly (alkylene oxide) polymers. In certain embodiments, the poly(alkylene oxide) is block copolymer of poly(ethylene glycol) and poly(propylene glycol). In other embodiments, the second side chain and the crosslinks both include poly(ethylene glycol).

In some embodiments, the first methacrylate-derived units can have the structure of formula (I):

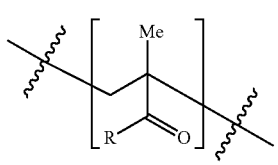

(I)

where R is a hydrophilic group. In certain embodiments, the hydrophilic group includes one or more hydroxy groups, such as an alcohol.

In some embodiments, the first methacrylate-derived units can have the structure of formula (Ia):

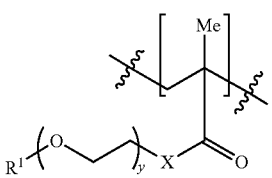

(Ia)

where X is —O—, —NR'— or —S—, y is 0, 1, 2, 3, 4, 5, 6, 7, 8, 9 or 10, and $R^1$ is hydrogen, —$C_1$-$C_{12}$alkyl, —$C_1$-$C_{12}$alkyl-OH, —$SiR'_3$, —C(O)—$C_1$-$C_{12}$alkyl, —$C_1$-$C_{12}$alkyl-C(O)OR', where R' is —$C_1$-$C_{12}$alkyl.

In certain embodiments, the first methacrylate-derived units have the structure:

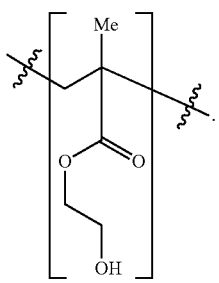

In some embodiments, the second methacrylate-derived units can have the structure of formula (II):

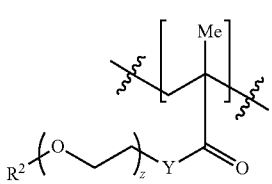

(II)

where Y is —O—, —NR'— or —S—, z is 0, 1, 2, 3, 4, 5, 6, 7, 8, 9 or 10, and $R^2$ is hydrogen, —$C_1$-$C_{12}$alkyl, —$SiR'_3$, —C(O)—$C_1$-$C_{12}$alkyl, —$C_1$-$C_{12}$alkyl-C(O)OR', where R' is hydrogen or —$C_1$-$C_{12}$alkyl.

In certain embodiments, z is an average value of from about 2 to about 250.

In some embodiments, the second methacrylate-derived units can have the structure of formula (IIa):

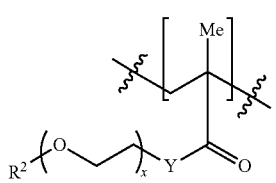

(IIa)

where Y and $R^2$ are as described above and x is such that the poly(ethylene glycol) has a number average molecular weight ($M_n$) of about 100 to about 10,000. In certain embodiments, x is selected so that the $M_n$ of the poly(ethylene glycol) falls within a range in Table 1.

TABLE 1

| $M_n$ range of poly(ethylene glycol) in the second methacrylate-derived units (values are approximate). | |
|---|---|
| Low | High |
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In certain embodiments, the analyte sensor has second methacrylate-derived units having the structure of formula (IIa), where Y is —O—, $R^2$ is methyl and x is such that the poly(ethylene glycol) has a number average molecular weight ($M_n$) of about 500.

In some embodiments, the presence of the second methacrylate-derived units having second hydrophilic side chains in the crosslinked, hydrophilic copolymer of the analyte sensor can form a porous network. The structure of the porous network includes regions within the copolymer that are not occupied by polymer, these regions are referred to herein as "pores". The porous network of the crosslinked, hydrophilic copolymer can facilitate control of the equilibrium between the concentration of the analyte (e.g., glucose) in the sample solution, and the analyte concentration in the proximity of the analyte sensor electrode surface. When all of the analyte arriving at the analyte sensor is consumed, the measured output signal can linearly proportional to the flow of the analyte and thus to the concentration of the analyte. However, when the analyte consumption is limited by the kinetics of chemical or electrochemical activities in the analyte sensor, the measured output signal may no longer be controlled by the flow of analyte and is no longer linearly proportional to the flow or concentration of the analyte. In this case, only a fraction of the analyte arriving at the analyte sensing component is consumed before the sensor becomes saturated, whereupon the measured signal stops increasing, or increases only slightly, with an increasing concentration of the analyte. The porous network can reduce the flow of the analyte to the analyte sensing component so the sensor does not become saturated and can therefore effectively enable a wider range of analyte concentrations to be measured.

The hydrophilic properties of the second side chain of the second methacrylate-derived units can be varied to produce desired properties of the porous network, such as permeability of the analyte. For example, flow of the analyte into or across the sensor can be dependent on the specific analyte being monitored, and thus, the porous network can be altered to obtain properties for monitoring a specific analyte. In some applications, the hydrophilicity of the porous network can be adjusted by changing the number alkylene oxide units in the second side chain. Similarly, the hydrophilicity of the porous network can be adjusted by modifying the ratio of carbon atoms (i.e., —C—, —CH—, —CH$_2$— or —CH$_3$) to alkylene oxide units in the second methacrylate-derived units.

In one embodiment, the cross-linked hydrophilic copolymer has a lower critical solution temperature (LCST) property within the body temperature range in water. Unlike a typical cross-linked polymer having a heat-expansion/cold contraction, the LCST property maintains gel swelling to a nearly constant degree within a certain temperature range, e.g., body temperature. For a biosensor membrane that regulates the analyte diffusion through the membrane, the LCST property ensures that the diffusion rate barely varies with temperature, resulting in a sensor having a sensitivity that does not change with temperature which is beneficial for continuous in vivo biosensors.

In some cases, by varying the chemical composition of monomers, the polymer temperature response in water can be controlled such that polymers with tunable LCST can be advantageously produced. The LCST property of the membranes may be attributed to the balance of the hydrophilic, e.g., PEGMA, and hydrophobic segments, e.g., hydrophobic polymer backbone, in the polymer chain. At lower temperatures, the hydrophilic interaction with water dominates and more water can be drawn into the network. When the temperature increases, the hydrophobic force slowly takes over and essentially "squeezes" water molecules in the network. This action drives out some water, thus cancelling a faster diffusion effect due to faster thermo-movements or faster diffusion of the analyte molecules at higher temperatures. The balance of the hydrophobic and hydrophilic actions keeps a nearly constant flux of analyte through the membrane at different temperatures In certain embodiments, the current produced by the sensor in response to the presence of an analyte may depend on the temperature coefficient for permeability to the analyte (such as glucose). For example, a membrane may be configured to have a temperature coefficient for permeability to an analyte (such as glucose) that is substantially zero. In these cases, the membrane is configured to have an analyte permeability to the analyte that does not substantially vary as the temperature changes, and thus the sensor is configured to produce a current that does not substantially vary as the temperature changes (assuming a constant concentration of analyte). In other cases, a membrane may be configured to have a low temperature coefficient for permeability to an analyte (such as glucose) such as less than 3% per degree Celsius, including less than 2% per degree Celsius, and less than 1% per degree Celsius. In these cases, the membrane is configured to have an analyte permeability to the analyte that does not substantially vary as the temperature changes, and thus the sensor is configured to produce a current that does not substantially vary as the temperature changes (assuming a constant concentration of analyte).

In other embodiments, the analyte sensor includes a membrane structure configured to have an analyte permeability that is substantially temperature independent. As such, in certain embodiments, the analyte sensor is configured to generate signals that are substantially temperature independent over a range of temperatures. That is, in certain instances, the analyte sensor is configured such that the signals generated by the analyte sensor do not depend on the temperature of the analyte sensor. For example, the analyte sensor may generate signals that are substantially temperature independent over a range of temperatures, where the range of temperatures is from 15 degrees Celsius to 50 degrees Celsius, such as from 20 degrees. Celsius to 40 degrees Celsius, including from 25 degrees Celsius to 45 degrees Celsius. Because the analyte sensor is configured to generate signals that are substantially temperature independent, in certain cases it is not necessary to correct the signals generated by the analyte sensor for changes in temperature. Thus, analyte sensors having temperature independent membranes may be used to determine a level of an analyte over a period of time without correcting for temperature variation at the sensor. For instance, determining the level of the analyte over a period of time may include monitoring the level of the analyte in a subject in the absence of correcting for temperature variation at the sensor. In addition, because the analyte sensor is configured to generate signals that are substantially temperature independent, in some cases embodiments of the analyte sensors do not include a temperature measurement device, such as a thermistor. In some cases, the sensor can be calibrated at room temperature without the need to correct signals generated by the analyte sensor for subsequent changes in temperature.

The term "temperature independent" means a value that does not substantially vary with changes in temperature. For example, the value may vary by 5% or less including 4% or less, or 3% or less, or 2% or less, or 1% or less per degree Celsius as the temperature changes. In some instances, analyte sensors that include a temperature independent membrane (e.g., analyte sensors that generate signals that are substantially temperature independent over a range of temperatures) generate signals over a temperature range that are within 95% or more of each other, for example within 96% or more of each other, or within 97% or more of each other, or within 98% or more of each other, or within 99% or more per degree Celsius of each other. In some cases, analyte sensors that include a temperature independent membrane generate signals over a temperature range that are within 90% or more of each other, for example within 95% or more of each other, or within 96% or more of each other, or within 97% or more of each other, or within 98% or more of each other, or within 99% or more per degree Celsius of each other over the temperature range at a constant analyte concentration. That is, the analyte sensor includes a membrane having an analyte permeability that is substantially temperature independent. The membrane has an analyte permeability to an analyte (such as glucose) that does not substantially vary with changes in temperature. For instance, the permeability of the membrane as a whole to an analyte (such as glucose) may vary by including 5% or less, or 2% or less, or 1% or less per degree Celsius as the temperature changes over the temperature range.

Permeability refers to a physical property of a substance that is related to the rate of diffusion of a permeate (e.g., a mobile substance) through the substance (e.g., a solid, semi-solid, gel, hydrogel, membrane, and the like). Permeability relates to the grade of transmissibility of the substance, meaning how much of the permeate diffuses through the substance in a specific time. In some instances, the permeability of a substance depends on the type of permeate, the concentration of the permeate, the size of the permeate, the pressure, the temperature, the type of substance, the thickness of the substance, the surface area of the substance, the pore size of the substance, the tortuosity of the substance, the density of the substance, and the like.

The term "permeability", as used herein, includes substances that are semi-permeable. Semi-permeability refers to the property of a material to be permeable only for some substances and not for others. For example, a semi-permeable membrane (also termed a selectively-permeable membrane, a partially-permeable membrane or a differentially-permeable membrane) is a membrane that will only allow certain molecules or ions to pass through it by diffusion. The rate of passage may depend on the pressure, concentration, and temperature of the molecules or solutes on either side, as well as the permeability of the membrane to each solute. Depending on the membrane and the solute, permeability may depend on solute size, solubility, other properties as described above, and the like. The analyte sensing component is embedded, i.e., surrounded by the polymer network of the crosslinked, hydrophilic copolymer. The embedded analyte sensing component is immobilized and can interact with a corresponding analyte of interest. In some embodiments, the analyte sensing component includes an enzyme.

The analyte sensing component of the analyte sensor can be selected to monitor physiological levels of a specific analyte. For example, glucose, lactate, cholesterol and various proteins and lipids can be found in body fluids, including, for example, tear film, and can be indicative of medical conditions that can benefit from continuous or semi-continuous monitoring.

The analyte sensing component can be an enzyme selected to monitor one or more analytes. For example, physiological cholesterol levels can be monitored with cholesterol oxidase, lactate levels with lactate oxidase, and glucose levels with glucose oxidase or glucose dehydrogenase (GDH).

In some embodiments, the analyte sensing component can be an enzyme that undergoes a chemical reaction with an analyte to produce detectable reaction products. For example, a copolymer including glucose oxidase ("GOx") can be situated around the working electrode to catalyze a reaction with glucose to produce hydrogen peroxide ($H_2O_2$). As shown below, the hydrogen peroxide can then be oxidized at the working electrode to releases electrons to the working electrode, which generates a current.

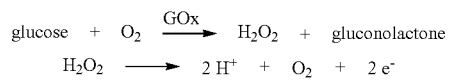

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

In other embodiments, the analyte sensing component is glucose dehydrogenase (GDH). In certain instances, the use of GDH can require the addition of a cofactor such as flavin adenine dinucleotide (FAD), nicotinamide adenine dinucleotide (NAD), flavin mononucleotide, pyrroloquinoline quinone (PQQ) or a coenzyme.

The crosslinks of the crosslinked, hydrophilic copolymer connect the third methacrylate-derived units in different backbone chains, and are represented by "A" in formula (III):

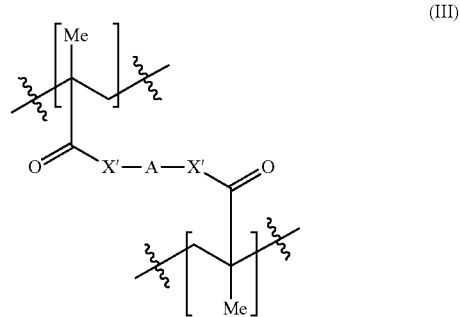

where X' is independently —O—, —NR'— or —S—, and A is a hydrophilic group.

In some embodiments, the crosslinks are hydrophilic. The crosslinks can be soluble in water or a water-miscible solvent, such as an alcohol. The crosslinks can have one or more heteroatoms, for example, nitrogen, oxygen or sulfur atoms. In some embodiments, the crosslinks have one or more hydroxy groups.

In some embodiments, the crosslinks include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the crosslinks is a block copolymer including blocks of two or three different poly(alkylene oxide) polymers. In certain embodiments, the poly(alkylene oxide) is a block copolymer of poly(ethylene glycol) and poly(propylene glycol). In other embodiments, the crosslinks and the second methacrylate-derived units include poly(ethylene glycol).

In some embodiments, the crosslinks include one or more ethylene oxide units. For example, the crosslinks (e.g., A in formula (III) above) can have the structure of formula (IIIa):

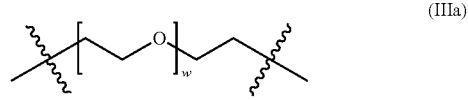

where w is 0, 1, 2, 3, 4, 5, 6, 7, 8, 9 or 10.

In certain embodiments, w is an average value of from about 2 to about 250.

In other embodiments, w in the crosslinks of formula (IIIa) is such that the number average molecular weight ($M_n$) of the PEG portion (within the brackets in formula (IIIa)) of the crosslinks is about 100 to about 10,000. For example, w can be selected such that the $M_n$ of the PEG portion of the crosslinks falls within a range in Table 2:

TABLE 2

| \multicolumn{2}{c}{$M_n$ range of the PEG portion of the crosslinks (values are approximate).} | |
|---|---|
| Low | High |
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In some embodiments, the crosslinks are derived from di(ethylene glycol)dimethacrylate, where w is 1.

The thickness of the crosslinked, hydrophilic copolymer of the analyte sensor can vary depending on the desired properties of the analyte sensor. The thickness of the copolymer, as measured from the top of electrode to the top of the copolymer, can play an important role in regulating the flow of the analyte to the analyte sensing component. Depending on the characteristics of the methacrylate-derived units in the copolymer the type of analyte sensing component used, and the analyte to be monitored, the thickness of the copolymer can be from less than about 10 μm to about 30 μm. In some instances, the copolymer is less than 20 μm in thickness, where in other applications the copolymer is about 20 μm to about 25 μm in thickness. In certain applications, the copolymer is about 10 μm to about 15 μm in thickness, where in other applications the copolymer is about 15 μm to about 20 μm or about 25 μm to about 30 μm in thickness. In some embodiments, the copolymer is about 20 μm in thickness.

In another aspect, a method for making an analyte sensor is disclosed. The method can involve:

a) forming a mixture including an analyte sensing component, a dimethacrylate monomer, an initiator, a first methacrylate monomer having a first hydrophilic side chain, and a second methacrylate monomer having a second hydrophilic side chain;

b) depositing the mixture onto a surface of an electrode; and c) subjecting the deposited mixture to conditions sufficient to initiate polymerization (i.e., curing) and form a crosslinked, hydrophilic copolymer, wherein the crosslinked, hydrophilic copolymer has an analyte permeability that is substantially temperature independent and wherein the analyte sensor generates signals that are substantially temperature independent over a range of temperatures.

In some embodiments of the method, the mixture is formed by combining three separate solutions. The method can involve:

a) forming a first solution which includes an analyte sensing component;

b) forming a second solution which includes a dimethacrylate monomer, an initiator, and a first methacrylate monomer having a first hydrophilic side chain;

c) forming a third solution which includes a dimethacrylate monomer, an initiator, and a second methacrylate monomer having a second hydrophilic side chain;

d) combining the three solutions to provide the mixture.

In some embodiments, the mixture can be formed on a surface of an electrode. For example, each component, or a combination of one or more components, can be individually deposited to form the mixture. Similarly, when the mixture is formed by combining three separate solutions, the solutions can combined on a surface of an electrode to form the mixture.

The ratio of the sensor precursors in the mixture can vary depending on the desired properties of the resulting analyte sensor. For example, adjusting the amount of the second methacrylate monomer having a second hydrophilic side chain can alter the porous network of the crosslinked, hydrophilic copolymer. Controlling the properties of the porous network can allow for the tuning of the permeability of the analyte sensor. Similar tunability can also be accomplished by adjusting the amount of the mixture deposited on the electrode, and/or adjusting the amount of the second methacrylate monomer combined with the first methacrylate monomer.

The mixture, or the first, second and third solutions can be formed in an aqueous medium, alcoholic medium, or mixture thereof. The aqueous medium can include a buffered aqueous solution, such as, for example, a solution containing citric acid, acetic acid, borate, carbonate, bicarbonate, 4-2-hydroxyethyl-1-piperazineethanesulfonic acid (HEPES), 3-{[tris(hydroxymethyl)methyl]amino}propanesulfonic acid (TAPS), N,N-bis(2-hydroxyethyl)glycine (Bicine), tris (hydroxymethyl)methylamine (Tris), N-tris(hydroxymethyl) methylglycine (Tricine), 3-[N-Tris(hydroxymethyl)methylamino]-2-hydroxypropanesulfonic acid (TAPSO), 2-{[tris (hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (MES), 2(R)-2-(methylamino)succinic acid, or phosphate buffered saline (PBS). In some embodiments, the mixture, or first, second and third solutions can be formed in a mixture of a buffered aqueous solution and ethanol.

In some embodiments of the method, the first, second and third solutions of the method can be formed with approximately the same concentration of analyte sensing component, first methacrylate monomer, and second methacrylate monomer, respectively. The percentage of each component can then be varied by adjusting the amounts each solution used to form the mixture. In some instances, the percentage of analyte sensing component in the mixture, is about 20% by weight to about 50% by weight, the percentage of first methacrylate monomer is 20% by weight to about 60% by weight, and the percentage of second methacrylate monomer is about 10% by weight to about 40% by weight. All percentages are given as a percentage of the cumulative amount of analyte sensing component, first methacrylate monomer and second methacrylate monomer. In certain examples, the percentage of analyte sensing component is about 40%, the amount of first methacrylate monomer is about 35% to about 40%, and the amount of second methacrylate monomer is about 20% to about 25%. In certain embodiments, the mixture is thoroughly mixed, optionally with a stirrer or shaker, before being deposited onto a surface of an electrode.

The analyte sensing component can be selected based on the analyte desired to be monitored. For example, to monitor physiological cholesterol levels, cholesterol oxidase can be used, and to monitor lactate levels lactate oxidase can be used. To monitor glucose levels, the analyte sensing component can include glucose oxidase or glucose dehydrogenase (GDH).

The analyte sensing component can be present during polymerization of the methacrylate and dimethacrylate monomers in the deposited mixture, such that polymerization of the methacrylate and dimethacrylate monomers results in the formation of a crosslinked, copolymer network in which the analyte sensing component is embedded. The embedded analyte sensing component is immobilized and can be used to monitor a corresponding analyte of interest.

The first and second methacrylate monomers include hydrophilic side chains that can have one or more heteroatoms. The first and second side chains can include one or more alkylene oxide units to form the crosslinked, hydrophilic copolymer of the analyte sensor as described herein.

In some embodiments of the method, the first methacrylate monomer has the structure of formula (IV):

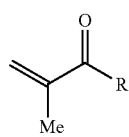

(IV)

where R is a hydrophilic group. In certain embodiments of the method, the hydrophilic group includes one or more hydroxy groups, such as an alcohol.

In some embodiments of the method, the first methacrylate monomer has the structure of formula (IVa):

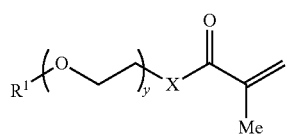

(IVa)

where X, y, $R^1$, and R' are selected to provide the first methacrylate-derived monomeric unit of the crosslinked, hydrophilic copolymer described herein.

In certain embodiments of the method, the first methacrylate monomer has the structure:

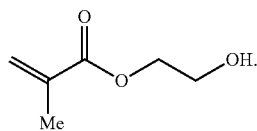

In some embodiments of the method, the second methacrylate monomer has the structure of formula (V):

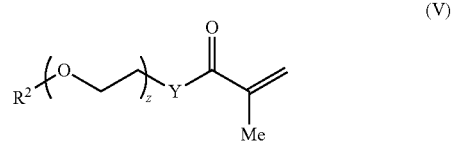

(V)

where Y, z, $R^2$ and R' are selected to provide the second methacrylate-derived monomeric unit of the crosslinked, hydrophilic copolymer described herein.

In some embodiments of the method, the second methacrylate monomer has the structure of formula (Va):

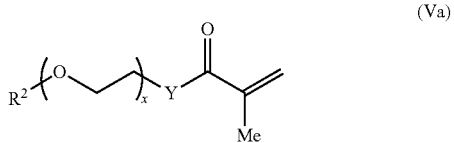

(Va)

where x is selected to provide second methacrylate-derived monomeric units of the crosslinked, hydrophilic copolymer described herein where the poly(ethylene glycol) has a number average molecular weight ($M_n$) of about 100 to about 10,000. In certain embodiments, x is selected to provide second methacrylate-derived monomeric units where the $M_n$ of the poly(ethylene glycol) falls within a range in Table 1.

In certain embodiments of the method, the second methacrylate monomer has the structure of formula (Va), where Y is —O—, $R^2$ is methyl and x is such that the poly(ethylene glycol) has a number average molecular weight ($M_n$) of about 500.

The dimethacrylate monomer is a molecule having two terminal methacrylate groups tethered by a hydrophilic linker. The hydrophilic linker is selected to provide the crosslinks between third methacrylate-derived units in different backbone chains of the crosslinked, hydrophilic copolymer described herein. In embodiments where the mixture is formed from the combination of two or more solutions each having a dimethacrylate monomer, the dimethacrylate monomers can be the same, or in some instances, can be different.

The extent of crosslinking in crosslinked, hydrophilic copolymer of the analyte sensor can be controlled by adjusting the amount of dimethacrylate monomer in the mixture. In some embodiments, the dimethacrylate monomer is about 1% to about 15% of the mixture. In other examples, the amount is about 1% to about 5%, or about 5% to about 10%, or about 10% to about 15%. In some embodiments, the amount is about 1%. In some instances, both the mixture includes about 1% of the dimethacrylate monomer.

In some embodiments of the method, the dimethacrylate monomer includes one or more alkylene oxide units to provide the crosslinks of the crosslinked, hydrophilic copolymer as described herein. In some embodiments, the dimethacrylate monomer includes poly(ethylene glycol) (PEG). For example, the dimethacrylate monomer can have the structure of formula (VI):

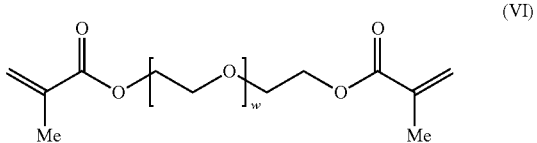

(VI)

where w is 0, 1, 2, 3, 4, 5, 6, 7, 8, 9 or 10.

In certain embodiments, w is an average value of from about 2 to about 250.

In other embodiments of the method, the dimethacrylate monomer can have the structure of formula (VI) where w is such that the number average molecular weight ($M_n$) of the PEG portion of the dimethacrylate monomer is about 100 to about 10,000. For example, w can be selected such that the $M_n$ of the PEG portion of the dimethacrylate monomer falls within a range in Table 2. In some embodiments, the dimethacrylate monomer is di(ethylene glycol)dimethacrylate.

Depositing the mixture onto a surface of an electrode can be accomplished by a number of methods. For example, the depositing can be performed manually with a micro-syringe, or by automated fabrication processes with nano jet dispensing equipment.

In some embodiments of the method, the amount of the mixture deposited onto a surface of an electrode is selected to provide the desired thickness of the crosslinked, hydrophilic copolymer of the analyte sensor. In some embodiments, the amount deposited on the electrode is about 50 $nL/mm^2$ to about 500 $nL/mm^2$. In other examples, the amount is about 50 µm to about 150 µm, or about 150 µm to about 300 µm, or about 300 µm to about 500 µm in thickness. In some embodiments, the amount is about 100 $nL/mm^2$. In some instances, depositing about 100 $nL/mm^2$ of the mixture provides a crosslinked, hydrophilic copolymer that is about 20 µm in thickness.

Conditions suitable to initiate polymerization (i.e., curing) can be selected based on the characteristics of the initiator and the monomers being polymerized, and as so not to degrade the analyte sensing component. In embodiments where the analyte sensing component is an enzyme, the temperature and pH of the method can be selected to preserve the activity of the enzyme. In certain embodiments the initiator is activated with ultraviolet (UV) light. For example, when 2,2-diemthoxy-2-phenylacetophenone is used as an initiator, curing can be performed with UV light. In embodiments where the mixture is formed from the combination of two or more solutions each having an initiator, the initiators can be the same, or in some instances, can be different.

In another aspect, a method for measuring the level of an analyte is a subject is provided. The method includes:

(a) mounting at least a portion of an analyte sensor onto the body of a subject, wherein the analyte sensor comprises: a crosslinked, hydrophilic copolymer in contact with a surface of an electrode; and an analyte sensing component embedded within the crosslinked, hydrophilic copolymer, wherein the crosslinked, hydrophilic copolymer comprises:

backbone chains comprising;

first methacrylate-derived units, each having a first hydrophilic side chain;

second methacrylate-derived units, each having a second hydrophilic side chain, wherein the first and second side chains are the same or different;

third methacrylate-derived units; and hydrophilic crosslinks between third methacrylate-derived units in different backbone chains, (b) determining the level of an analyte over a period of time from signals generated by the analyte sensor, wherein the crosslinked, hydrophilic copolymer has an analyte permeability that is substantially temperature independent and wherein the analyte sensor generates signals that are substantially temperature independent over a range of temperatures.

In one embodiment, the method employs a body-mountable device that includes an analyte sensor. An example of a body-mountable device comprising an eye-mountable device that is configured to detect at least one analyte in a tear film of a user wearing the eye-mountable device will now be described in greater detail.

Figure 4:
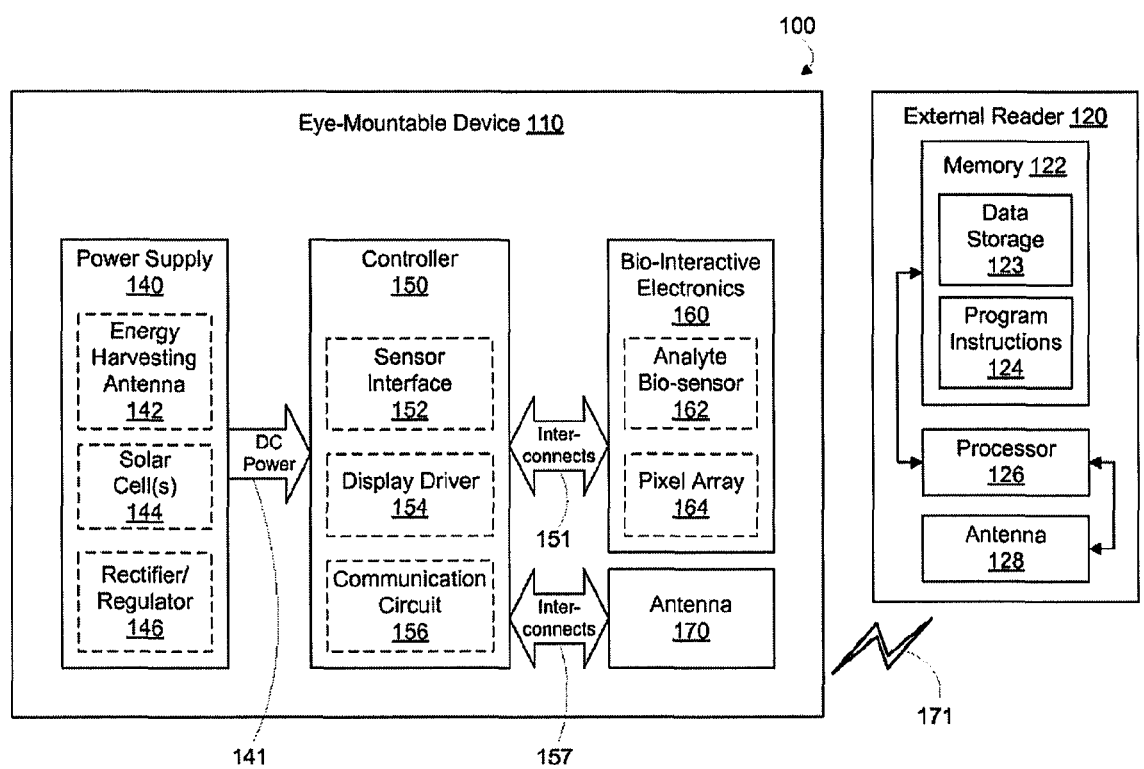
FIG. 4 is a block diagram of a system with an eye-mountable device in wireless communication with an external reader, according to an example embodiment.

FIG. 4 is a block diagram of a system 100 that includes an eye-mountable device 110 in wireless communication with an external reader 120. The eye-mountable device 110 may be a polymeric material that may be appropriately shaped for mounting to a corneal surface and in which a structure is at least partially embedded. The structure may include a power supply 140, a controller 150, bio-interactive electronics 160, and an antenna 170.

In some embodiments, the structure may be a bio-compatible device in which some or all of the components formed or mounted thereon are encapsulated by a bio-compatible material.

In some example embodiments, the structure may be positioned away from the center of the eye-mountable device 110 and thereby avoid interference with light transmission to the central, light-sensitive region of the eye. For example, where the eye-mountable device 110 is shaped as a curved disk, the structure may be embedded around the periphery (e.g., near the outer circumference) of the disk. In other example embodiments, the structure may be positioned in or near the central region of the eye-mountable device 110. For example, portions of the structure may be substantially transparent to incoming visible light to mitigate interference with light transmission to the eye. Moreover, in some embodiments, the bio-interactive electronics 160 may include a pixel array 164 that emits and/or transmits light to be received by the eye according to display instructions. Thus, the bio-interactive electronics 160 may optionally be positioned in the center of the eye-mountable device so as to generate visual cues perceivable to a wearer of the eye-mountable device 110, such as displaying information (e.g., characters, symbols, flashing patterns, etc.) on the pixel array 164.

The power supply 140 is configured to harvest ambient energy to power the controller 150 and bio-interactive electronics 160, and may include an energy harvesting antenna 142 and/or solar cells 144. The energy harvesting antenna 142 may capture energy from incident radio radiation. The solar cells 144 may comprise photovoltaic cells configured to capture energy from incoming ultraviolet, visible, and/or infrared radiation.

A rectifier/regulator 146 may be used to condition the captured energy to a stable DC supply voltage 141 at a level suitable for operating the controller, and then supply the voltage to the controller 150. The rectifier/regulator 146 may include one or more energy storage devices to mitigate high frequency variations in the energy harvesting antenna 142 and/or solar cell(s) 144. For example, one or more energy storage devices (e.g., a capacitor or an inductor) may be connected in parallel across the outputs of the rectifier/regulator 146 to regulate the DC supply voltage 141 and may be configured to function as a low-pass filter.

The controller 150 is configured to execute instructions to operate the bio-interactive electronics 160 and the antenna 170. The controller 150 includes logic circuitry configured to operate the bio-interactive electronics 160 so as to interact with a biological environment of the eye-mountable device 110. The interaction could involve the use of one or more components, such an analyte bio-sensor 162 in the bio-interactive electronics 160, to obtain input from the biological environment. Additionally or alternatively, the interaction could involve the use of one or more components, such as a pixel array 164, to provide an output to the biological environment.

In one example, the controller 150 includes a sensor interface module 152 that is configured to operate the analyte bio-sensor 162. The analyte bio-sensor 162 may be, for example, an amperometric electrochemical sensor that includes a working electrode and a reference electrode driven by a sensor interface. A voltage is applied between the working and reference electrodes to cause an analyte to undergo an electrochemical reaction (e.g., a reduction and/or oxidation reaction) at the working electrode. The electrochemical reaction generates an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent may also be included to sensitize the electrochemical sensor to one or more desired analytes. For example, a layer of glucose oxidase ("GOD") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode as discussed above.

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 may also include a display driver module 154 for operating a pixel array 164. The pixel array 164 is an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 may also include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 may also include a communication circuit 156 for sending and/or receiving information via the antenna 170. The communication circuit 156 may include one or more oscillators, mixers, frequency injectors, or the like to modulate and/or demodulate information on a carrier frequency to be transmitted and/or received by the antenna 170. In some example embodiments, the eye-mountable device 110 is configured to indicate an output from a bio-sensor by modulating an impedance of the antenna 170 in a manner that is perceivable by the external reader 120. For example, the communication circuit 156 can cause variations in the amplitude, phase, and/or frequency of backscatter radiation from the antenna 170, and such variations may then be detected by the reader 120.

The controller 150 is connected to the bio-interactive electronics 160 via interconnects 151. Similarly, the controller 150 is connected to the antenna 170 via interconnects 157. The interconnects 151, 157 may comprise a patterned conductive material (e.g., gold, platinum, palladium, titanium, copper, aluminum, silver, metals, any combinations of these, etc.).

It is noted that the block diagram shown in FIG. 4 is described in connection with functional modules for convenience in description. However, embodiments of the eye-mountable device 110 can be arranged with one or more of the functional modules ("sub-systems") implemented in a single chip, integrated circuit, and/or physical component.

Additionally or alternatively, the energy harvesting antenna 142 and the antenna 170 can be implemented in the same, dual-purpose antenna. For example, a loop antenna can both harvest incident radiation for power generation and communicate information via backscatter radiation.

The external reader 120 includes an antenna 128 (or group of more than one antennae) to send and receive wireless signals 171 to and from the eye-mountable device 110. The external reader 120 also includes a computing system with a processor 126 in communication with a memory 122. The memory 122 is a non-transitory computer-readable medium that can include, without limitation, magnetic disks, optical disks, organic memory, and/or any other volatile (e.g., RAM) or non-volatile (e.g., ROM) storage system readable by the processor 126. The memory 122 includes a data storage 123 to store indications of data, such as sensor readings (e.g., from the analyte bio-sensor 162), program settings (e.g., to adjust behavior of the eye-mountable device 110 and/or external reader 120), etc. The memory 122 also includes program instructions 124 for execution by the processor 126. For example, the program instructions 124 may cause the external reader 120 to provide a user interface that allows for retrieving information communicated from the eye-mountable device 110 (e.g., sensor outputs from the analyte bio-sensor 162). The external reader 120 may also include one or more hardware components for operating the antenna 128 to send and receive the wireless signals 171 to and from the eye-mountable device 110. For example, oscillators, frequency injectors, encoders, decoders, amplifiers, and filters can drive the antenna 128 according to instructions from the processor 126.

The external reader 120 may be a smart phone, digital assistant, or other portable computing device with wireless connectivity sufficient to provide the wireless communication link 171. The external reader 120 may also be implemented as an antenna module that can be plugged in to a portable computing device, such as in an example where the communication link 171 operates at carrier frequencies not commonly employed in portable computing devices. In some instances, the external reader 120 is a special-purpose device configured to be worn relatively near a wearer's eye to allow the wireless communication link 171 to operate using little or low power. For example, the external reader 120 can be integrated in a piece of jewelry such as a necklace, earring, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. To perform a reading with the system 100 configured as a tear film analyte monitor, the external reader 120 can emit radio frequency radiation 171 that is harvested to power the eye-mountable device 110 via the power supply 140. Radio frequency electrical signals captured by the energy harvesting antenna 142 (and/or the antenna 170) are rectified and/or regulated in the rectifier/regulator 146 and a regulated DC supply voltage 141 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 120 (e.g., via the communication circuit 156).

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 120 to the eye-mountable device 110 to request a measurement. By periodically interrogating the eye-mountable device 110 (e.g., by supplying radio frequency radiation 171 to temporarily turn the device on) and storing the sensor results (e.g., via the data storage 123), the external reader 120 can accumulate a set of analyte concentration measurements over time without continuously powering the eye-mountable device 110.

Figure 5A:
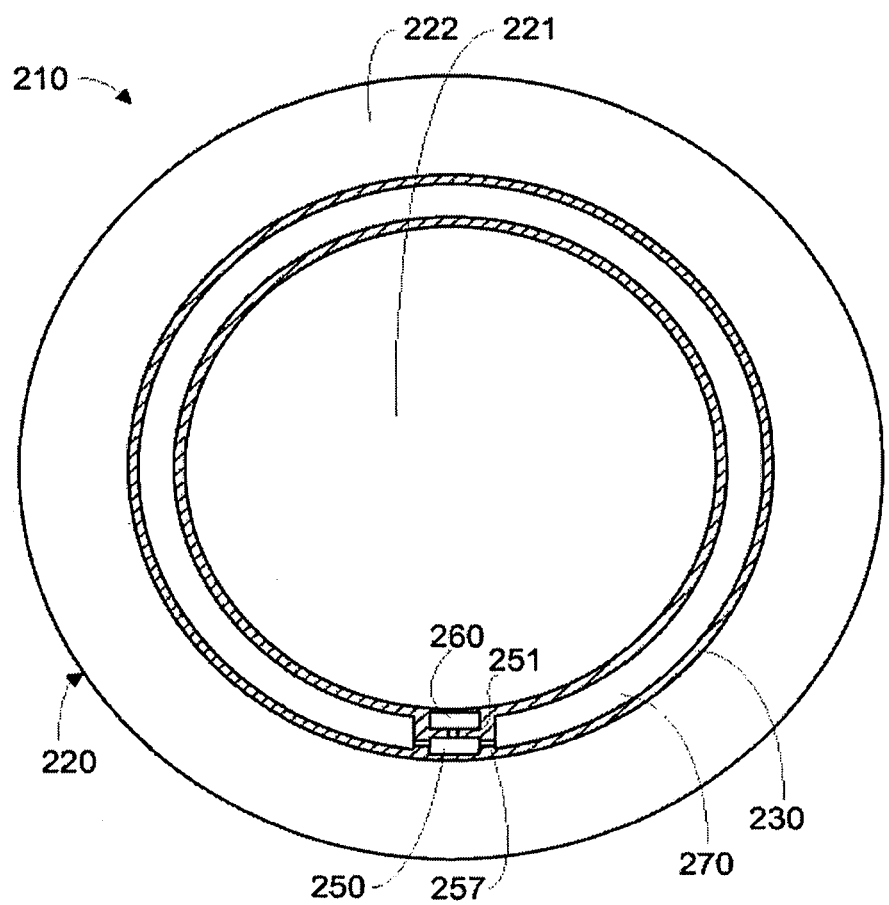
FIG. 5a is a top view of an eye-mountable device, according to an example embodiment.
Figure 5B:
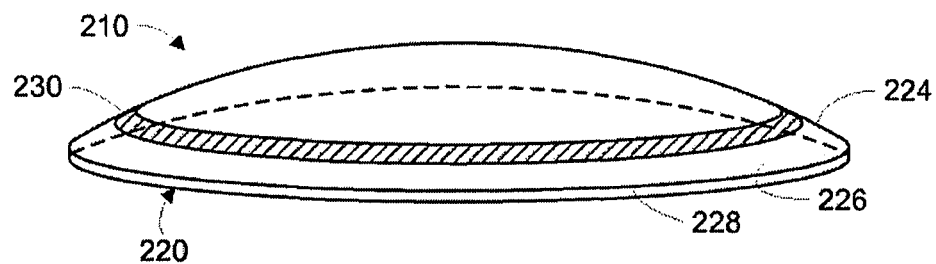
FIG. 5b is a side view of an eye-mountable device, according to an example embodiment.

FIG. 5a is a top view of an eye-mountable device 210. FIG. 5b is side view of the eye-mountable device 210. It is noted that relative dimensions in FIGS. 5a and 5b are not necessarily to scale, but have been rendered for purposes of explanation only in describing the arrangement of the eye-mountable device 210.

The eye-mountable device 210 may include a polymeric material 220, which may be a substantially transparent material to allow incident light to be transmitted to the eye. The polymeric material 220 may include one or more bio-compatible materials similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, or any combinations of these. Other polymeric materials may also be envisioned. The polymeric material 220 may include materials configured to moisturize the corneal surface, such as hydrogels and the like. In some embodiments, the polymeric material 220 is a deformable ("non-rigid") material to enhance wearer comfort.

To facilitate contact-mounting, the eye-mountable device 210 may comprise a concave surface 226 configured to adhere ("mount") to a moistened corneal surface (e.g., by capillary forces with a tear film coating the corneal surface). While mounted with the concave surface against the eye, a convex surface 224 of eye-mountable device 210 is formed so as not to interfere with eye-lid motion while the eye-mountable device 210 is mounted to the eye. A circular outer side edge 228 connects the concave surface 224 and the convex surface 226. The convex surface 224 can therefore be considered an outer, top surface of the eye-mountable device 210 whereas the concave surface 226 can be considered an inner, bottom surface. The "top" view shown in FIG. 5a is facing the convex surface 224.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 may be selected according to the size and/or shape of the corneal surface and/or the scleral surface of the wearer's eye. In some embodiments, the eye-mountable device 210 is shaped to provide a predetermined, vision-correcting optical power, such as provided by a prescription contact lens.

A structure 230 is embedded in the eye-mountable device 210. The structure 230 can be embedded to be situated near or along an outer periphery 222, away from a central region 221. Such a position ensures that the structure 230 will not interfere with a wearer's vision when the eye-mountable device 210 is mounted on a wearer's eye, because it is positioned away from the central region 221 where incident light is transmitted to the light-sensing portions of the eye. Moreover, portions of the structure 230 can be formed of a transparent material to further mitigate effects on visual perception.

The structure 230 may be shaped as a flat, circular ring (e.g., a disk with a centered hole). The flat surface of the structure 230 (e.g., along the radial width) allows for mounting electronics such as chips (e.g., via flip-chip mounting) and for patterning conductive materials to form electrodes, antenna(e), and/or interconnections. The structure 230 and the polymeric material 220 may be approximately cylindrically symmetric about a common central axis. The structure 230 may have, for example, a diameter of about 10 millimeters, a radial width of about 1 millimeter (e.g., an outer radius 1 millimeter greater than an inner radius), and a thickness of about 50 micrometers. These dimensions are provided for example purposes only, and in no way limit this disclosure.

A loop antenna 270, controller 250, and bio-interactive electronics 260 are included in the structure 230. The controller 250 may be a chip including logic elements configured to operate the bio-interactive electronics 260 and the loop antenna 270. The controller 250 is electrically connected to the loop antenna 270 by interconnects 257 also situated on the structure 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) may be formed from any type of conductive material and may be patterned by any process that can be used for patterning such materials, such as deposition or photolithography, for example. The conductive materials patterned on the structure 230 may be, for example, gold, platinum, palladium, titanium, carbon, aluminum, copper, silver, silver-chloride, conductors formed from noble materials, metals, or any combinations of these materials. Other materials may also be envisioned.

The structure 230 may be a bio-compatible device in which some or all of the components are encapsulated by a bio-compatible material. In one example, the controller 250, interconnects 251, 257, bio-interactive electronics 260, and the loop antenna 270 are fully encapsulated by bio-compatible material, except for the sensor electrodes in the bio-interactive electronics 260.

As shown in FIG. 5a, the bio-interactive electronics module 260 is on a side of the structure 230 facing the convex surface 224. Where the bio-interactive electronics module 260 includes an analyte bio-sensor, for example, mounting such a bio-sensor on the structure 230 to be close to the convex surface 224 allows the bio-sensor to sense analyte that has diffused through convex surface 224 or has reached the bio-sensor through a channel in the convex surface 224 (FIGS. 5c and 5d show a channel 272).

The loop antenna 270 is a layer of conductive material patterned along the flat surface of the structure 230 to form a flat conductive ring. In some example embodiments, the loop antenna 270 does not form a complete loop. For example, the loop antenna 270 may include a cutout to allow room for the controller 250 and bio-interactive electronics 260, as illustrated in FIG. 5a. However, in another example embodiment, the loop antenna 270 can be arranged as a continuous strip of conductive material that wraps entirely around the structure 230 one or more times. Interconnects between the ends of such a wound antenna (e.g., the antenna leads) can connect to the controller 250 in the structure 230. In some embodiments, the loop antenna can include a plurality of conductive loops spaced apart from each other, such as three conductive loops, five conductive loops, nine conductive loops, etc. With such an arrangement, the polymeric material 220 may extend between adjacent conductive loops in the plurality of conductive loops.

Figure 5C:
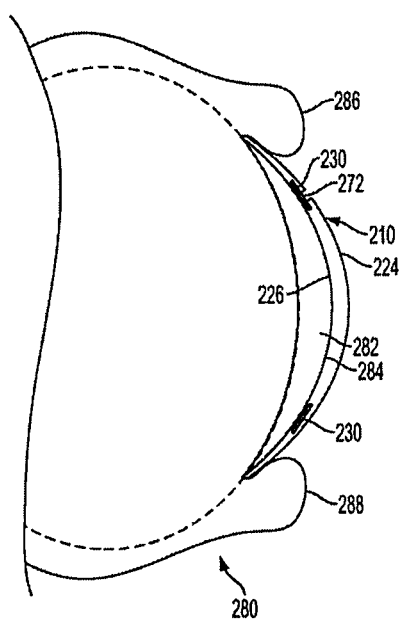
FIG. 5c is a side cross-section view of the eye-mountable device of FIG. 5a while mounted to a corneal surface of the eye, according to an example embodiment.
Figure 5D:
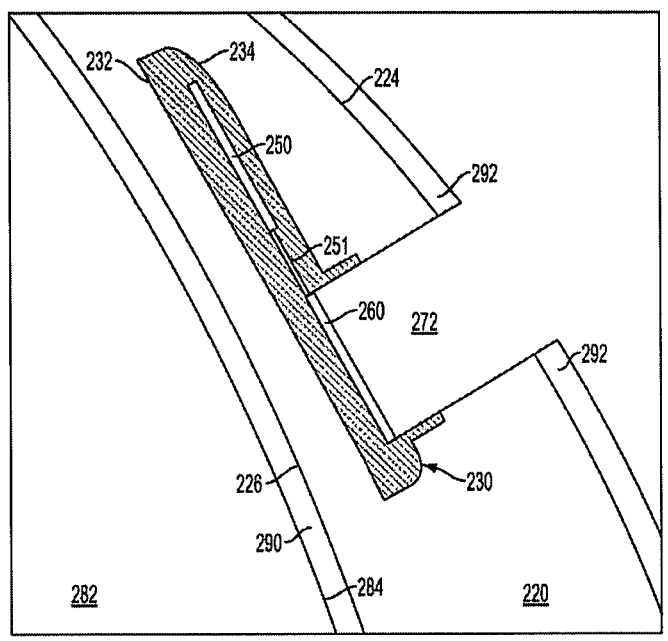
FIG. 5d is a side cross-section view showing the tear film layers surrounding the surfaces of the eye-mountable device mounted as shown in FIG. 5c, according to an example embodiment.

FIG. 5c is a side cross-section view of the eye-mountable electronic device 210 mounted to a corneal surface 284 of an eye 280. FIG. 5d is an enlarged partial view of the cross-section of the eye-mountable device shown in FIG. 5c. It is noted that relative dimensions in FIGS. 5c and 5d are not necessarily to scale, but have been rendered for purposes of explanation only in describing the arrangement of the eye-mountable device 210. Some aspects are exaggerated to allow for illustration and to facilitate explanation.

The eye 280 includes a cornea 282 that is covered by bringing an upper eyelid 286 and a lower eyelid 288 together over the surface of the eye 280. Incident light is received by the eye 280 through the cornea 282, where light is optically directed to light sensing elements of the eye 280 to stimulate visual perception. The motion of the upper and lower eyelids 286, 288 distributes a tear film across the exposed corneal surface 284 of the eye 280. The tear film is an aqueous solution secreted by the lacrimal gland to protect and lubricate the eye 280. When the eye-mountable device 210 is mounted in the eye 280, the tear film coats both the concave and convex surfaces 224, 226, providing an inner layer 290 (along the concave surface 226) and an outer layer 292 (along the convex surface 224). The inner layer 290 on the corneal surface 284 also facilitates mounting the eye-mountable device 210 by capillary forces between the concave surface 226 and the corneal surface 284. In some embodiments, the eye-mountable device 210 can also be held over the eye 280 in part by vacuum forces against the corneal surface 284 due to the curvature of the concave surface 226. The tear film layers 290, 292 may be about 10 micrometers in thickness and together account for about 10 microliters of fluid.

The tear film is in contact with the blood supply through capillaries in the structure of the eye and includes many biomarkers found in blood that are analyzed to diagnose health states of an individual. For example, tear film includes glucose, calcium, sodium, cholesterol, potassium, other biomarkers, etc. The biomarker concentrations in tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body.

As shown in the cross-sectional views in FIGS. 5c and 5d, the structure 230 can be inclined so as to be approximately parallel to the adjacent portion of the convex surface 224. As described above, the structure 230 is a flattened ring with an inward-facing surface 232 (closer to the concave surface 226 of the polymeric material 220) and an outward-facing surface 234 (closer to the convex surface 224). The structure 230 can include electronic components and/or patterned conductive materials adjacent to either or both surfaces 232, 234.

As shown in FIG. 5d, the bio-interactive electronics 260, the controller 250, and the conductive interconnect 251 are located between the outward-facing surface 234 and the inward-facing surface 632 such that the bio-interactive electronics 260 are facing the convex surface 224. With this arrangement, the bio-interactive electronics 260 can receive analyte concentrations in the tear film 292 through the channel 272. However, in other examples, the bio-interactive electronics 260 may be mounted on the inward-facing surface 232 of the structure 230 such that the bio-interactive electronics 260 are facing the concave surface 226.

While the body-mountable device has been described as comprising the eye-mountable device 110 and/or the eye-mountable device 210, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 110 and/or the eye-mountable device 210. For instance, the tooth-mountable device could include a polymeric material that is the same as or similar to any of the polymeric materials described herein and a structure that is the same as or similar to any of the structures described herein. With such an arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 110 and/or the eye-mountable device 210. For instance, the skin-mountable device could include a polymeric material that is the same as or similar to any of the polymeric materials described herein and a structure that is the same as or similar to any of the structures described herein. With such an arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

EXAMPLES

Example 1

Immobilization of GOx in a Crosslinked Methacrylate Copolymer

Three solutions (A-C) were prepared:
A) 25 mg/ml glucose oxidase (GOx) in PBS buffer (pH=7.4)
B) 2-hydroxyethyl methacrylate monomer solution containing 1% by weight di(ethylene glycol)dimethacrylate and 1% by weight 2,2-dimethoxy-2-phenylacetophenone.
C) poly(ethylene glycol) methyl ether methacrylate (average Mn 500, Aldrich product #447943) monomer solution containing 1% by weight di(ethylene glycol)dimethacrylate and 1% by weight 2,2-dimethoxy-2-phenylacetophenone.

Two formulations (F2 and F4) were prepared by combining a volume of each solution (A-C) according to the ratios in the following table:

|  | A | B | C |
|---|---|---|---|
| Formulation F2 | 0.40 | 0.40 | 0.20 |
| Formulation F4 | 0.40 | 0.35 | 0.25 |

The resulting formulations were thoroughly mixed with a vortex shaker. A micro-syringe was used to deposit 100 nL/mm$^2$ of each formulation onto a sensor electrode, and the deposited solution was UV-cured for 5 minutes at 365 nm under nitrogen with an EC-500 light exposure chamber (Electro-Lite Corp). The resulting cured crosslinked copolymers each had a thickness of about 20 μm. The sensor made with Formulation F4, used a greater ratio of solution C to solution B than Formulation F2. Thus, the sensor made with Formulation F4 has a greater ratio of poly(ethylene glycol) methyl ether methacrylate-derived units to 2-hydroxyethyl methacrylate-derived units than the sensor made with Formulation F2.

Example 2

Analyte Sensor Performance in a Glucose Solution

The analyte sensors of Formulation F2 and F4 formed in Example 1 were tested at concentrations of glucose in phosphate buffered saline (PBS) ranging from 50 μM to 1000 μm. Both sensors were submerged in PBS and the glucose concentration was increased every 10-15 minutes. The current generated at the electrode was measured using a potentiostat. A linear relationship between current and glucose concentration was observed for both formulations (See inset, FIG. 1). The sensor made with Formulation F4, which was a greater ratio of poly(ethylene glycol) methyl ether methacrylate-derived units to 2-hydroxyethyl methacrylate-derived units than the sensor made with Formulation F2, had a higher current response at the same concentration of glucose than the sensor made with Formulation F2. See FIG. 1.

Example 3

Effect of Temperature on Analyte Sensor Current Response

Figure 2A:
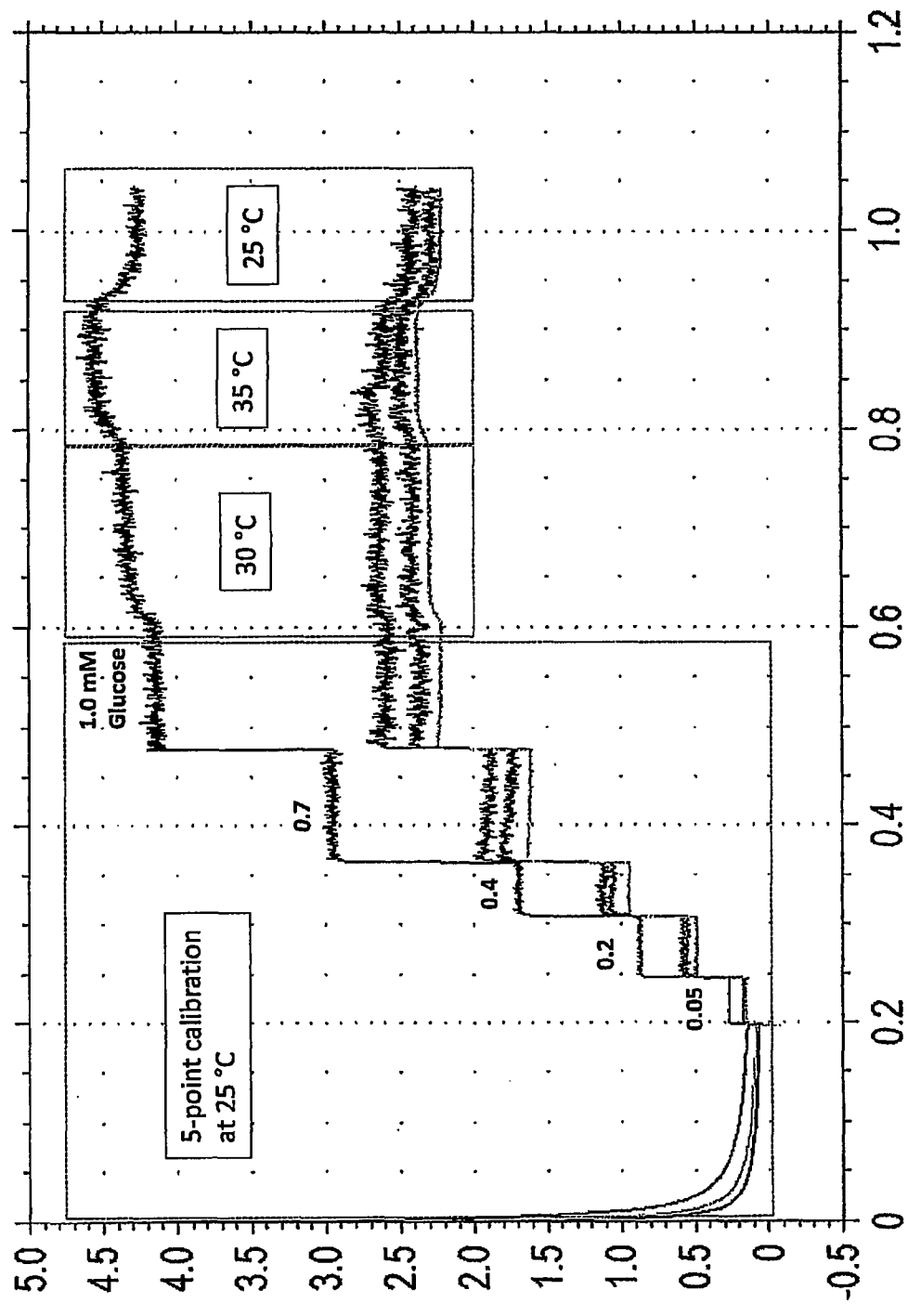
FIG. 2(a) is a graph of current produced by four glucose sensors at glucose concentrations of 50 μM, 200 μM, 400 μM, 700 μM and 1,000 μM in phosphate buffered saline (PBS) at temperatures of 25 degrees Celsius. For glucose concentration of 1000 μM, the current was also measured at 30 degrees Celsius and 35 degrees Celsius.

Four analyte sensors of Formula F1 (the ratio of the three stock solutions A:B:C=0.4:0.45:0.15) were prepared in accordance with the procedure of Example 1 and were tested at various concentrations of glucose in phosphate buffered saline (PBS) ranging from 50 μM to 1000 μm at 25 degrees Celsius following the procedure of Example 2. As shown in FIGS. 2(*a*) and 2(*b*), a linear relationship between current and glucose concentration was observed for all four analyte sensors. When current was measured for 1.0 mM glucose concentration at 25, 20, and 35 degree Celsius, the temperature effect on the current response was minimal or negligible (<1% per degree Celsius), demonstrating the temperature insensitivity of the analyte sensor.

Example 4

Effect of Temperature on Analyte Sensor Current Response

Figure 3:
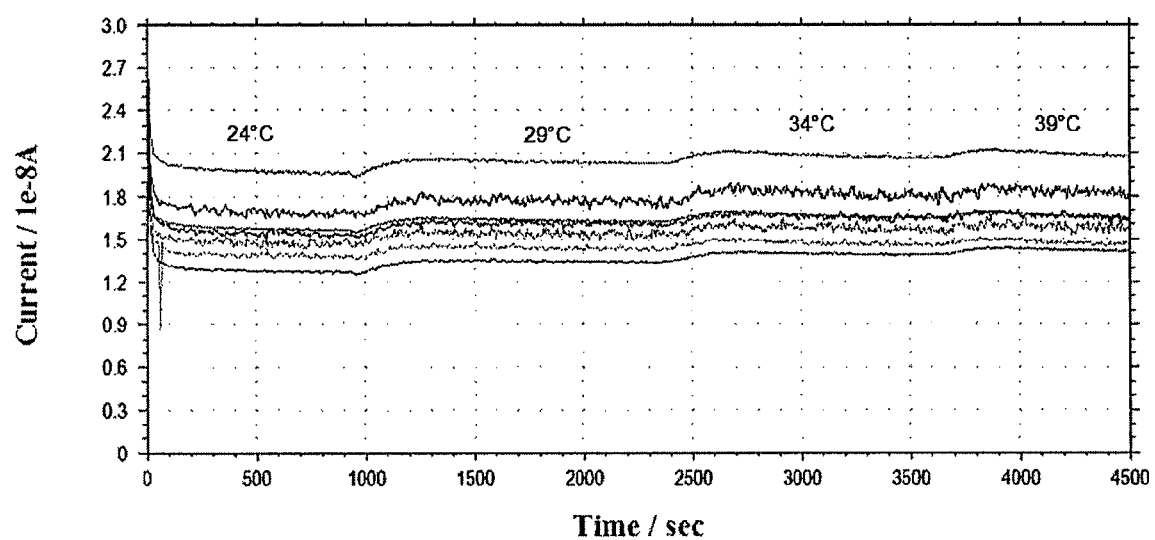
FIG. 3 is a graph of current produced by seven glucose sensors at glucose concentration of 1000 μM at temperatures of 24, 29, 34 and 39 degrees Celsius. The temperature effect on the current response was minimal or negligible (<1% per degree Celsius), demonstrating the temperature insensitivity of the analyte sensors

In this Example, essentially Example 3 was repeated with a wider temperature range. Seven analyte sensors of Formula F1 were prepared in accordance with the procedure of Example 1 and were tested in 1 mM glucose solution in PBS at various temperatures. As shown in FIG. 3, when current was measured for 1.0 mM glucose concentration at increasing temperatures 24, 29, 34 and 39 degrees Celsius, the temperature effect on the current response was again minimal or negligible (<1% per degree Celsius), demonstrating the temperature insensitivity of the analyte sensor.

Although the crosslinked, hydrophilic copolymers in the above examples comprise methacrylate groups, there are a number of ethylenically unsaturated groups known in the art to be capable of undergoing polymerization. Ethylenically unsaturated monomers and macromers may be either acrylic- or vinyl-containing Vinyl-containing monomers contain the vinyl grouping ($CH_2=CH-$), and are generally highly reactive. Acrylic-containing monomers are represented by the formula:

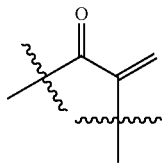 [SMILES: *C(=C)C(*)=O]

Examples of suitable polymerizable groups may include acrylic-, ethacrylic-, itaconic-, styryl-, acrylamido-, methacrylamido- and vinyl-containing groups such as the allyl group.

In addition to the above disclosed methods of forming crosslinked, hydrophilic copolymers by the polymerization of ethylenically unsaturated monomers and macromonomers, additional chemistries will be known to one or ordinary skill in the art to from such copolymers. As an example, epoxy chemistry, in which multifunctional amines and multifunctional epoxy compounds are mixed together and cured, can be used to form crosslinked, hydrophilic copolymers. Additionally, urethane chemistry may be used, in which multifunctional isocyanates are mixed with multifunctional alcohols and cured to provide crosslinked, hydrophilic copolymers. Other chemistries for the formation of crosslinked, hydrophilic copolymers exist, and will be well known to those of ordinary skill in the art.

It should be understood that arrangements described herein are for purposes of example only. As such, those skilled in the art will appreciate that other arrangements and other elements (e.g., machines, interfaces, functions, orders, and groupings of functions, etc.) can be used instead, and some elements can be omitted altogether according to the desired results. Further, many of the elements that are described are functional entities that can be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

The invention claimed is:

1. A glucose sensor comprising:
a crosslinked, hydrophilic copolymer in contact with a surface of an electrode; and
a glucose sensing component embedded within the crosslinked, hydrophilic copolymer, wherein the crosslinked, hydrophilic copolymer comprises:
backbone chains comprising;
first methacrylate-derived units, each having a first hydrophilic side chain;
second methacrylate-derived units, each having a second hydrophilic side chain,
wherein the first and second side chains are the same or different;
third methacrylate-derived units; and
hydrophilic crosslinks between third methacrylate-derived units in different backbone chains, wherein the crosslinked, hydrophilic copolymer has glucose permeability that is substantially temperature independent, wherein the analyte sensor generates signals that are substantially temperature independent over a range of temperatures, and wherein the glucose sensor can measure a glucose concentration of 1000 uM or less.

2. The sensor according to claim 1, wherein the crosslinked, hydrophilic copolymer has a temperature coefficient that is less than 1%/° C.

3. The sensor according to claim 1, wherein the signals generated by the sensor are within 90% or more of each other over the temperature range at a constant glucose concentration.

4. The sensor according to claim 1, wherein the first methacrylate-derived units have the structure of formula (Ia):

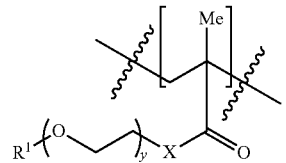

wherein
X is —O—, —NR'— or —S—;
y is 0-10; and
$R^1$ is hydrogen, —$C_1$-$C_{12}$alkyl, —$C_1$-$C_{12}$alkyl-OH, —SiR'$_3$, —C(O)—$C_1$-$C_{12}$alkyl, —$C_1$-$C_{12}$alkyl -C(O) OR', wherein R' is —$C_1$-$C_{12}$alkyl.

5. The sensor according to claim 1, wherein the first methacrylate-derived units have the structure:

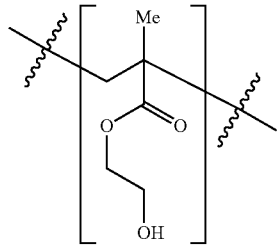

6. The sensor according to claim 1, wherein the second methacrylate-derived units have the structure of formula (II):

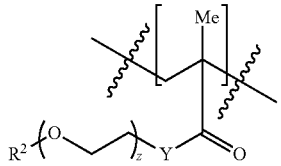
(II)

wherein
Y is —O—, —NR'— or —S—;
R$^2$ is hydrogen, —C$_1$-C$_{12}$alkyl, —SiR'$_3$, —C(O)—C$_1$C$_{12}$alkyl, —C$_1$-C$_{12}$alkyl-C(O)OR', where R' is hydrogen or -C$_1$-C$_{12}$alkyl; and
z is 0-10.

7. The sensor according to claim 1, wherein the second methacrylate-derived units have the structure of formula: (II):

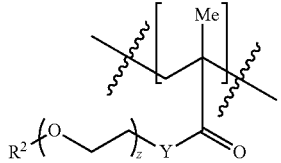
(II)

wherein
Y is —O—, —NR'— or —S—;
R$^2$ is hydrogen, —C$_1$-C$_{12}$alkyl, —SiR'$_3$, —C(O)—C$_1$-C$_{12}$alkyl, —C$_1$-C$_{12}$alkyl-C(O)OR', where R' is hydrogen or —C$_1$-C$_{12}$alkyl; and
z is an average value of from 2 to about 250.

8. The sensor according to claim 1, wherein the hydrophilic crosslinks have the structure of formula (IIIa):

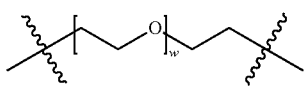
(IIIa)

wherein w is 0-10.

9. The sensor according to claim 1, wherein the hydrophilic crosslinks have the structure of formula (IIIa):

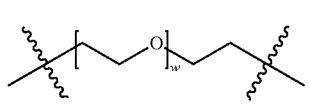
(IIIa)

wherein w is an average value of from about 2 to about 250.

10. The sensor according to claim 1, wherein the glucose sensing component comprises glucose oxidase.

11. The sensor according to claim 1, wherein the cross-linked, hydrophilic copolymer has a thickness of about 20μm.

12. The sensor according to claim 1, wherein
the first methacrylate-derived units are derived from 2-hydroxyethylmethacrylate;
the second methacrylate-derived units have the structure of formula (II):

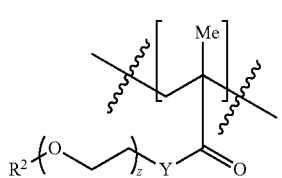
(II)

wherein z is an average value of from about 10 to about 15;
the hydrophilic crosslinks have the structure of formula (IIIa):

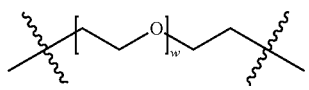
(IIIa)

wherein w is 2; and
the glucose sensing component comprises glucose oxidase.

13. The sensor according to claim 1, wherein the range of temperatures is from 25° C. to 35° C.

* * * * *